United States Patent
Everett et al.

(10) Patent No.: US 7,382,464 B2
(45) Date of Patent: Jun. 3, 2008

(54) APPARATUS AND METHOD FOR COMBINED OPTICAL-COHERENCE-TOMOGRAPHIC AND CONFOCAL DETECTION

(75) Inventors: Matthew J. Everett, Livermore, CA (US); Yan Zhou, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 122 days.

(21) Appl. No.: 11/298,105

(22) Filed: Dec. 9, 2005

(65) Prior Publication Data

US 2006/0158655 A1  Jul. 20, 2006

Related U.S. Application Data

(60) Provisional application No. 60/645,434, filed on Jan. 20, 2005.

(51) Int. Cl.
*G01B 9/02* (2006.01)

(52) U.S. Cl. .................................. 356/479

(58) Field of Classification Search .......... 356/479, 356/73, 477, 497, 478; 385/127, 126
See application file for complete search history.

(56) References Cited

U.S. PATENT DOCUMENTS

| | | | | |
|---|---|---|---|---|
| 4,869,593 A | | 9/1989 | Biegen | 356/351 |
| 5,321,501 A | | 6/1994 | Swanson et al. | 356/345 |
| 5,459,570 A | | 10/1995 | Swanson et al. | 356/345 |
| 5,926,592 A | * | 7/1999 | Harris et al. | 385/33 |
| 5,975,697 A | * | 11/1999 | Podoleanu et al. | 351/206 |
| 6,014,215 A | * | 1/2000 | Kempen et al. | 356/479 |
| 6,485,413 B1 | | 11/2002 | Boppart et al. | 600/160 |
| 6,769,769 B2 | | 8/2004 | Podoleanu et al. | 351/206 |

(Continued)

FOREIGN PATENT DOCUMENTS

WO   WO 01/42735 A1   6/2001

(Continued)

OTHER PUBLICATIONS

In re U.S. Appl. No. 11/219,992, filed Sep. 6, 2005, by Robert W. Knighton et al., entitled Enhanced optical coherence tomography for anatomical mapping.

(Continued)

*Primary Examiner*—Tarifur R Chowdhury
*Assistant Examiner*—Jonathan M Hansen
(74) *Attorney, Agent, or Firm*—Stallman & Pollock LLP

(57) ABSTRACT

This invention provides a better apparatus and method for the generation of Optical Coherence Tomography (OCT) and Confocal Scanning Laser Ophthalmoscope (CSLO) images, using a dual-waveguiding module. A dual-waveguiding structure consists of a single-mode and a multi-mode waveguide each with optimum size and numerical aperture for highly efficient collection of the OCT and CSLO optical signals. Separation of the two signals is achieved by channeling most of the multi-mode guided optical power to a CSLO detector. The non-tapped single-mode guided optical wave is further sent to a pure single-mode fiber of a standard OCT system for OCT image generation. The present invention achieves highly efficient optical power usage and hence high signal to noise ratio, together with inherent pixel-to-pixel registration of the OCT and CSLO images, and a cost reduction of the OCT/CSLO combo system.

25 Claims, 5 Drawing Sheets

U.S. PATENT DOCUMENTS

| | | | |
|---|---|---|---|
| 2002/0071647 A1 | 6/2002 | Manzur | 385/127 |
| 2003/0199769 A1 | 10/2003 | Podoleanu et al. | 600/476 |
| 2004/0036838 A1 | 2/2004 | Podoleanu et al. | 351/206 |
| 2004/0233457 A1 | 11/2004 | Podoleanu et al. | 356/479 |
| 2005/0140984 A1 | 6/2005 | Hitzenberger | 356/497 |

FOREIGN PATENT DOCUMENTS

| | | |
|---|---|---|
| WO | WO 2004/073501 A2 | 9/2004 |

OTHER PUBLICATIONS

A.G. Podoleanu et al., "Simultaneous en-face imaging of two layers in the human retina by low-coherence reflectometry," *Optics Letters*, vol. 22, No. 13, Jul. 1, 1997, pp. 1039-1041.

A.G. Podoleanu et al., "En-face coherence imaging using galvanometer scanner modulation," *Optics Letters*, vol. 23, No. 3, Feb. 1, 1998, pp. 147-149.

A.G. Podoleanu et al., "Transversal and Longitudinal Images from the Retina of the Living Eye Using Low Coherence Reflectometry," *Journal of Biomedical Optics*, vol. 3, No. 1, Jan. 1998, pp. 12-20.

A.G. Podoleanu et al., "Combined optical coherence tomograph and scanning laser ophthalmoscope," *Electronics Letters*, vol. 34, No. 11, May 28, 1998, pp. 1088-1090.

A.G. Podoleanu et al., "Noise Analysis of a Combined Optical Coherence Tomograph and a Confocal Scanning Ophthalmoscope," *Applied Optics*, vol. 38, No. 10, Apr. 1, 1999, pp. 2116-2127.

J.G. Fujimoto et al., "Optical Coherence Tomography: An Emerging Technology for Biomedical Imaging and Optical Biopsy," *Neoplasia*, vol. 2, Nos. 1-2, Jan.-Apr. 2000, pp. 9-25.

A.M. Rollins et al., "Emerging Clinical Applications of Optical Coherence Tomography," *Optics and Photonics News*, vol. 13, No. 4, Apr. 2002, pp. 36-41.

J.G: Fujimoto, "Optical coherence tomography for ultrahigh resolution in vivo imaging," *Nature Biotechnology*, vol. 21, No. 11, Nov. 2003, pp. 1361-1367.

C.K. Hitzenberger et al., "Three-dimensional imaging of the human retina by high-speed optical coherence tomography," *Optics Express*, vol. 11, No. 21, Oct. 20, 2003, pp. 2753-2761.

A.G. Podoleanu et al., "Sequential optical coherence tomography and confocal imaging," *Optics Letters*, vol. 29, No. 4, Feb. 15, 2004, pp. 364-366.

A.G. Podoleanu et al., "Combined multiplanar optical coherence tomography and confocal scanning ophthalmoscopy," *Journal of Biomedical Optics*, vol. 9, No. 1, Jan./Feb. 2004, pp. 86-93.

P.F. Sharp et al., "The scanning laser ophthalmoscope—a review of its role in bioscience and medicine," *Physics in Medicine and Biology*, vol. 49, (2004), pp. 1085-1096.

D. Yelin et al., "Double-clad fiber for endoscopy," *Optics Letters*, vol. 29, No. 20, Oct. 15, 2004, pp. 2408-2410.

A.G. Podoleanu et al., "Combined multiplanar optical coherence tomography and confocal scanning ophthalmoscopy," *Journal of Biomedical Optics*, vol. 9, No. 1, Jan./Feb. 2004, pp. 86-93.

* cited by examiner

APPARATUS AND METHOD FOR COMBINED OPTICAL-COHERENCE-TOMOGRAPHIC AND CONFOCAL DETECTION

PRIORITY

This application claims priority from U.S. Provisional Application Ser. No. 60/645,434, filed Jan. 20, 2005, the disclosure of which is incorporated herein by reference.

FIELD OF THE INVENTION

This invention relates to optical imaging and diagnostic devices, specifically to devices that image depth-dependent structures in semi-transparent tissue. The invention provides a device to efficiently record both the optical coherence tomography (OCT) image and a high-quality confocal en-face image, this en-face image showing precisely the region scanned by the OCT measurement.

BACKGROUND AND PRIOR ART

In optical imaging of biological tissues, especially the living human eye, it has been shown in recent years that both OCT and confocal scanning laser imaging systems have particular individual advantages.

On one hand, OCT provides a high axial imaging resolution of the order of about 10 microns which is determined by the coherence length of the light source used. This technology is particularly useful for diagnostics that requires high depth resolution tomographic imaging [Fujimoto, J. G. et al. (2000) "Optical Coherence Tomography: An Emerging Technology for Biomedical Imaging and Optical Biopsy" *Neoplasia*, 2, 9-25; Rollins A. M. et al. (2002) "Emerging Clinical Applications of Optical Coherence Tomography" *Optics and Photonics News*, 13(4): 36-41; Fujimoto, J. G. (2003) "Optical coherence tomography for ultrahigh resolution in vivo imaging." *Nat Biotechnol* 21(11): 1361-1367]. Meanwhile, attempts have also been made to produce en-face OCT images that look like the retinal images from an ophthalmoscope for anatomic mapping of a biological sample [Podoleanu, A. G., G. M. Dobre, et al. (1997). "Simultaneous en-face imaging of two layers in the human retina by low-coherence reflectometry." *Optics Letters* 22(13): 1039-1041; Podoleanu, A. G., G. M. Dobre, et al. (1998). "En-face coherence imaging using galvanometer scanner modulation." *Optics Letters* 23(3): 147-149]. However, one disadvantage associated with an OCT image is that the image is very fragmented and is sometimes difficult to interpret, leading to difficulty in terms of identifying anatomic structures.

On the other hand, confocal scanning laser imaging has been successfully applied to retinal imaging and is now well accepted by ophthalmologists in imaging the anatomic structures of the retina [see for example, Sharp, P. F. et al (2004) "The scanning laser ophthalmoscope—a review of its role in bioscience and medicine" *Physics in Medicine and Biology* 49: 1085-1096]. As the depth resolution of a CSLO is determined by the depth of focus of the confocal optics, a CSLO has a typical axial resolution of about 300 microns.

It was realized some years ago that a simultaneous generation of both an OCT image and a CSLO image having a pixel-to-pixel registration correspondence would not only offer the advantages of both imaging techniques but also solve the two problems of registering a three dimensional (3D) OCT image to en-face images of the same tissue, and of correcting for OCT image distortion caused by the movement of the sample such as an eye. This is because in order to generate a 3D OCT data set of a sample, it is necessary to properly register each slice of many transverse scans (B-scans) or en-face scans (C-scans) which may be misaligned due to the sample movement in between each scans and then stack them accordingly. Therefore, a simultaneous generation of both an OCT image and a CSLO image with pixel-to-pixel registration correspondence is especially useful.

One of the major benefits of combining OCT and CSLO is that they have different depth ranges. In principle OCT can be used to measure optical reflectivity at a dense set of points covering a volume of interest, and then the OCT data can be reduced to simulate the en-face image that would be seen by a CSLO or other ophthalmoscope. However OCT collection optics generally collect less sample-returned light than do CSLO collection optics. As is well known in the art, OCT is an interference-based technique so only light that is spatially coherent contributes to the signal. Often the sample-returned light is collected for OCT in a single-mode optical fiber. Reflected light which does not couple into that single mode, either by falling outside the fiber core or by entering at too steep an angle, is rejected.

Often the greater part by far of the light reflected from the sample is rejected in this way.

Nevertheless, attempts have been made to directly use the OCT configuration to generate both an OCT image and a CSLO image. In a first approach, the reference light of an OCT interferometer was alternately temporarily blocked to generate a CSLO signal, and restored to generate an OCT signal. However, this approach results in sequential, rather than simultaneous, acquisition of the OCT and CSLO images. Attempts were also made to directly use the OCT signal without blocking the OCT reference arm to simultaneously create, in addition to an OCT image, an anatomic structure image with an appearance similar to that of a CSLO image. In this respect, one approach involves the integration, or superposition on top of one another, of a multiple number of the standard OCT signals along the depth dimension. This integration is used to obtain an averaged overall depth reflectivity for each transverse pixel to generate an en-face image [Hitzenberger, C. K. et al. (2003). "Three-dimensional imaging of the human retina by high-speed optical coherence tomography." *Optics Express* 11(21): 2753-2761]. Another approach uses multiple light sources of different coherence lengths to simultaneously generate multiple OCT images of different depth resolutions. Still another approach uses low pass electronic filtering of the OCT signal to extract a CSLO-like image.

All these techniques to directly use the OCT configuration to generate both an OCT image and a CSLO image collect light through a small pin-hole defined by the core size of a single mode fiber (of the order of 10 micron with a small numerical aperture (NA) as compared to the standard size of a CSLO pin-hole size of about 100 micron with a generally larger NA), which leads to a low signal to noise ratio for the CSLO image. Another problem associated with these approaches is that the forward propagating light can be relatively strongly reflected by the fiber end and sent to the confocal detector with a strength greater than the sample returned signal light, causing the CSLO sample signal being overwhelmed by the fiber end reflection.

A second approach that addresses the above problems is to separate the OCT and CSLO signals returned from the sample using a plate beam-splitter. Part of the returned sample light is directed to a separate pin hole for CSLO signal generation. Such a design can get rid of the problem of reflections from the fiber end, simultaneously produce the desired two images, enable the optimization of the CSLO signal to noise ratio by choice of the pin-hole size, and allow use of the same transverse scanner for both the OCT beam and the CSLO beam. Registration between the OCT and confocal images can be achieved with optical alignment of the respective detectors and the free-space beam splitter. However, due to the fact that a certain percentage of the returned sample beam is now deflected to the confocal pin-hole, there is a reduction in the OCT signal strength. Meanwhile, a significant amount of the returned sample beam is lost in the cladding of the OCT single mode fiber, which light could have been used for CSLO imaging.

It is desirable to have a solution that both overcomes the above-mentioned limitations and also reduces the cost of the system. It is clear from the-above analysis that the key issue is to optimize the optical power efficiency for the two images so that the signal to noise ratio for both the OCT and the CSLO images can approach the maximum achievable values as offered by each stand-alone system.

In this invention, a novel dual-waveguiding module is disclosed for both highly efficient collection as well as highly efficient separation of the OCT and CSLO signals. As a result of the present invention, highly efficient optical power usage and hence high signal to noise ratio are achieved together with inherent pixel-to-pixel registration of the OCT and CSLO images and a cost reduction of an OCT/CSLO combo system. In a preferred embodiment of the invention, a concentric single-mode/multi-mode dual-waveguiding structure (e.g. a double-clad fiber) is used to simultaneously collect both the sample returned OCT and CSLO optical signals with almost the same efficiency as can be achieved by each stand-alone device. Extraction and separation of the two signals is achieved by channeling most of the multi-mode guided optical power to a CSLO detector, using single or multiple stage multi-mode coupling or other optical power extraction techniques. The non-tapped single-mode guided optical wave is further sent to a standard OCT system for OCT image generation. With this invention, the numerical aperture and the pin-hole size for the CSLO signal can be optimized for a maximum signal to noise ratio nearly as good as can be achieved in a stand-alone CSLO system, while there is no reduction to the OCT signal strength.

SUMMARY OF THE INVENTION

The present invention discloses an apparatus and a method for the generation of Optical Coherence Tomography (OCT) and confocal Scanning Laser Ophthalmoscope (CSLO) signals, using a dual-waveguiding module consisting of a dual-waveguiding structure and a multi-mode optical power extractor.

In one aspect of the invention, a combined OCT and confocal detection apparatus for the generation with high efficiency of an OCT and a confocal image is constructed from a dual-waveguiding structure that has at least two waveguides, one for single mode waveguiding and the other for multi-mode waveguiding, and a multi-mode optical power extractor made along the dual-waveguiding structure. The light from a light source is coupled to the sample through the single mode waveguide of the dual-waveguiding structure. The sample-returned light is separately collected by the single mode waveguide and the multi-mode waveguide. The multi-mode optical power is extracted and directed to a photo detector for CSLO signal generation, whereas the single mode guided optical wave in the dual-waveguiding structure is coupled to a single mode fiber based OCT system for OCT signal generation.

In another aspect of the invention, a method is disclosed for obtaining an OCT and a CSLO image with high signal to noise ratios. The method comprises coupling the light from a source to a sample through a single mode fiber, generating a confocal image from light returning to the fiber end but not coupled into the single mode core of the fiber, and generating an OCT image from the sample returned light that is coupled to the single mode core of the fiber.

A first object of the present invention is to simultaneously collect the OCT signal and/or the CSLO signal in two concentric waveguides, and to also effectively separate these two signals using a multi-mode optical power extractor, for the generation of high quality OCT and CSLO images that have pixel-to-pixel correspondence. With the present invention, the strength of both the OCT signal and the CSLO signal can be preserved as in each stand-alone system and the CSLO signal to noise ratio can be optimized by controlling the CSLO confocal detection pin-hole size.

A second object of the invention is to reduce the cost and the complexity of a combined OCT/CSLO system. This is achieved through the use of the same transverse scanner for both the OCT beam and the CSLO beam and also the use of commercially available double-clad fiber and multi-mode fiber coupler which are less expensive than bulk optics and simplify optical alignment.

A third object of the invention is to substantially reduce the amount of illumination light reflected from the fiber end back into the CSLO detector. This can be achieved by angle-polishing the end of the double-clad fiber so that the reflected light is deflected to beyond the numerical aperture of the single mode and multi-mode waveguide. As an alternative approach, the dual-waveguiding structure can be connected to a refractive-index-matched bulk optic; this approach allows more space in the design to avoid sending light reflected from its surfaces into the CLSO detector. An anti-reflection coating may be applied to all the optical interfaces to further reduce reflection.

Another object of the invention is to capture more sample-returned CSLO light by using a larger numerical aperture for the multi-mode waveguide of the dual-waveguiding structure and match it with the numerical aperture of the confocal optics in a probe module that serves optical beam focusing and scanning functions.

These and other features and advantages of the present invention will become more readily apparent to those skilled in the art upon review of the following detailed description of the preferred embodiments taken in conjunction with the accompanying drawings.

DETAILED DESCRIPTION AND PREFERRED EMBODIMENT

The present invention discloses an apparatus and a method for coupling source light through a single mode fiber to a sample, collecting and separating spatially coherent light for an interferometric measurement, and collecting and separating spatially incoherent light for imaging. The interferometric measurement produces an OCT image, and the spatially incoherent light is used to form a CSLO image. The two images can be obtained independently, sequentially or simultaneously, with high quality, using a dual-waveguiding module consisting of a dual-waveguiding optical structure that may be combined with a multi-mode optical power extractor. Although a dual-waveguiding structure has been used for spectrally encoded scanning laser imaging [Yelin, D. et al. (2004). "Double-clad fiber for endoscopy." *Optics Letters* 29(20): 2408-2410], such a structure has not been combined with OCT to simultaneously produce both an OCT image and a confocal image. In a preferred embodiment, a concentric dual-waveguiding structure consisting of both a single mode waveguide and a multi-mode waveguide is employed and optimized to simultaneously capture the sample-returned optical signal for both images. The amount of light captured in the single-mode waveguide is the same as that captured in a stand-alone OCT system. The amount of light captured in the multi-mode waveguide for CLSO is slightly less than in a stand-alone CSLO with equivalent pinhole size, as the part of the light reflected from the sample is routed instead to the OCT system. The two captured signals are then separated, with the multi-mode guided optical power being extracted through multi-mode coupling and sent to the CLSO detector, and the single-mode guided optical power being coupled to an OCT system.

Figure 1:
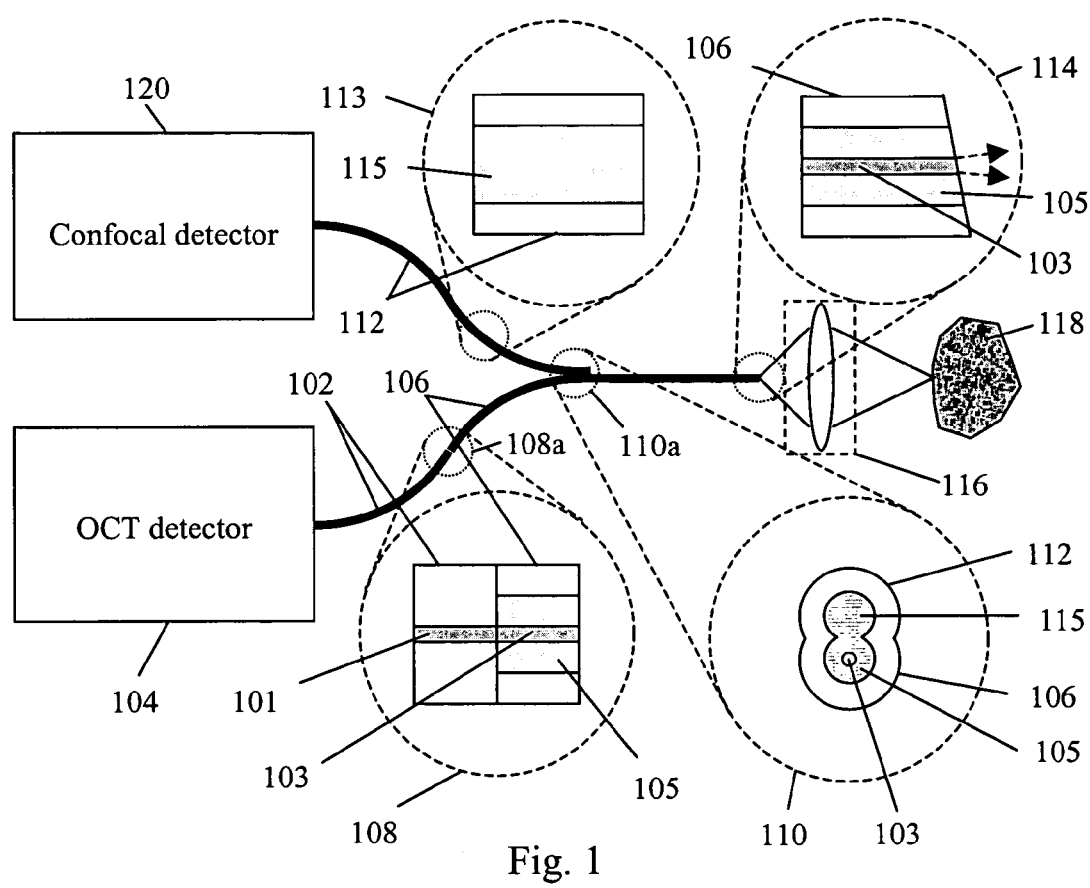
FIG. 1 is a schematic diagram that shows a preferred embodiment of the dual-waveguiding optical detection module.

FIG. 1 shows a schematic diagram of one preferred embodiment of the present invention. Light guided from the core 101 of the single mode fiber 102 of an OCT system 104 is optically connected to the inner core single-mode waveguide 103 of a concentric double-clad fiber 106. As shown in the inset 108 of the interconnection region between the pure single-mode fiber 102 and the double-clad fiber 106, it is preferred that the optical mode profile of the single-mode fiber 102 is well-matched to that of the inner core of the double-clad fiber 106 and the two fibers are fuse-spliced together with good alignment so that there is a minimum loss of single mode optical power in both the forward and reverse propagation directions. However, it should be noted that this is not absolutely required as optical fibers of different mode profiles and other optical connection means such as the use of optical fiber connector can also be employed.

Light guided by the inner core 103 of the double-clad fiber 106 will propagate through the multi-mode coupling region (see inset 110) with little loss of the inner-core-guided optical power due to the fact that the multi-mode coupling region, as shown by the transverse cross-sectional view of inset 110, will only enable optical power coupling of the multi-mode guided light between the outer core 105 of the double-clad fiber 106 and the multi-mode core 115 of the pure multimode fiber 112 (also see inset 113 for an enlarged longitudinal cross section view of the pure multi-mode fiber). The inner core guided light will hence continue to propagate to the end of the double-clad fiber 106 and leave the double-clad fiber slightly divergently (see inset 114). A probe module 116, that may serve light beam collimation, scanning and focusing functions, etc., may be used to direct and focus the forward propagating light beam to the sample 118. It is preferred that the double-clad fiber end as shown by inset 116 is angle-polished and also anti-reflection coated so that there is a minimum reflection of the forward propagating optical power being captured and guided by the inner core and/or the outer core of the double-clad fiber. Note that in this respect, the angle required will generally be larger than that for a pure single mode fiber if the outer core of the double clad fiber has a larger numerical aperture (NA).

Figure 2A:
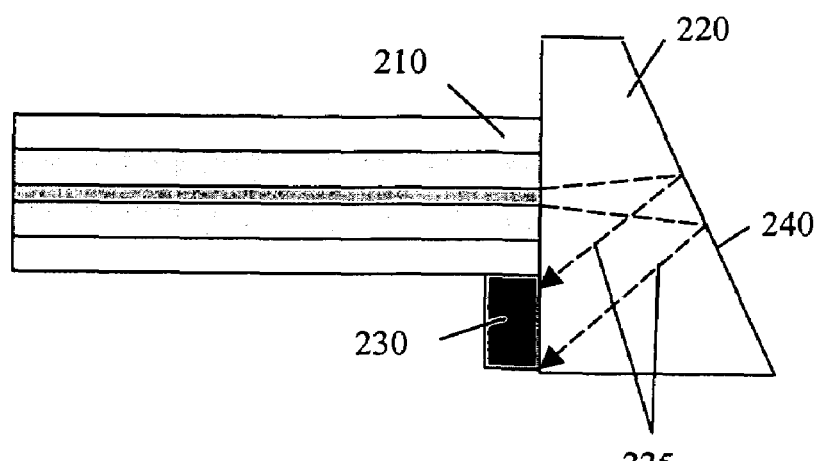
FIG. 2a shows an example of connecting a flat end double-clad fiber to a refractive-index-matched prism for deflecting the reflected light off the capturing zone of the double-clad fiber.
Figure 2B:
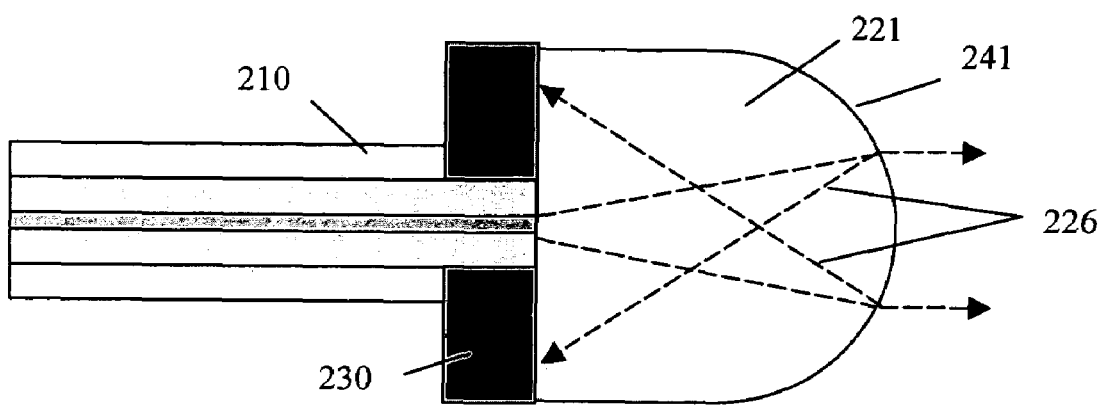
FIG. 2b shows an example of connecting a flat end double-clad fiber to a collimator lens for deflecting the reflected light off the capturing zone of the double-clad fiber.

It should be understood that angle-polishing the double-clad fiber end is only one exemplary way of minimizing the capturing and guiding of fiber end reflected light. There are various other ways to shape the fiber end or to connect the fiber end with other optical element of various shapes to achieve the same goal. FIG. 2a shows an example of connecting a non-angled double-clad fiber 210 to a refractive-index-matched prism 220 for deflecting the reflected light 225 off the capturing zone of the double-clad fiber 220. Note that in this example, index matching material may be used between the double-clad fiber 210 and the prism 220, and light absorbing material 230 may also be used to absorb the optical interface reflected light. As configured, the light absorbing material can function as a pin-hole aperture for controlling the numerical aperture of collection. Anti-reflection coating may also be deposited on the angled beam exit prism face 240. Alternatively, FIG. 2b shows an example of connecting a double-clad fiber 210 to a refractive-index-matched collimator lens 221. Some light 226 is reflected from surface 241, but at a wide range of angles so that very little couples back into fiber 210.

Figure 2C:
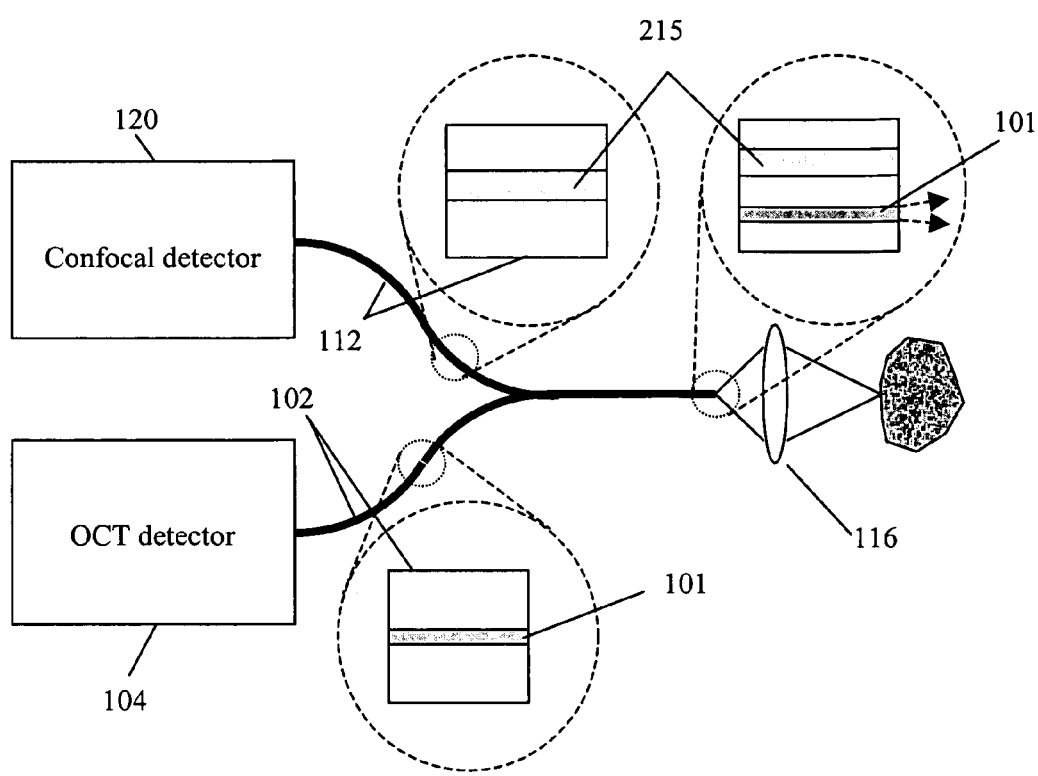
FIG. 2c shows an example of using a double-cored fiber in one alternative embodiment of the dual-waveguiding optical detection module.

Another alternative, shown in FIG. 2c, is to displace the waveguide collecting light for the CSLO from the waveguide used for illumination and collection of the OCT light. This design could use a double-cored fiber for the two waveguides. The CSLO collecting waveguide 215 is adjacent to the OCT waveguide 101, and preferably as close as it practical, so that the collecting waveguide 215 lies within the image formed by optics 116 of the illuminated portion of the sample. The collection of light for the CSLO is less efficient in this design, and there is a small offset between OCT and SLO images, but for practical purposes the registration problem is solved because the offset is constant. In this embodiment, the collection waveguide 215 can be either a single mode fiber or a multi-mode fiber.

Referring back to FIG. 1, light returned from the sample 118 through scattering/reflection, or other means such as fluorescence, is collected and focused by the same probe module 116 back to the double-clad fiber end (114). It should be noted, however, that while the single-mode part of the double-clad fiber end collects light in basically the same way as in other OCT systems using pure single mode fiber, the multi-mode portion of the double-clad fiber end has a much larger area and can now collect much more light returned from the sample with a larger numerical aperture and from a larger sample volume as determined by the confocal optics. The outer core 105 of the double-clad fiber now offers a number of flexibilities in terms of optimizing the CSLO signal. The numerical aperture (NA) of the outer core 105 can be designed, independently from that of the inner core, to match the NA of the optics in probe module 116 so that more sample returned light can now be captured by the multi-mode waveguide for CSLO imaging. In addition, the diameter of the outer core 105 can directly function as the detection pin-hole of the confocal system and can be optimized to provide a high signal to noise ratio for the CSLO signal. Alternatively, with a large enough outer core diameter, an additional mask with a pin-hole can be placed in front of the double-clad fiber and serve as the adjustable pin-hole size for CSLO signal optimization. Note that the sample-returned light collected in the multimode waveguide is not part of the OCT optical signal and therefore, the OCT signal strength is preserved as in a stand-alone OCT system. In fact, since the amount of returned sample light collected by the inner core 103 is generally only a tiny fraction of the light collected in the multi-mode waveguide due to the generally smaller NA and the much smaller surface area of the inner core 103, if the multi-mode guided light can be separated from the single-mode guided light and efficiently channeled to a confocal detector, this invention will achieve a CSLO signal to noise ratio almost as high as what a stand-alone CSLO system can offer. The improved efficiency of light collection also makes the CSLO signal relatively larger than the reflection of illuminating light from the fiber end.

Note that due to the concentric nature of the double-clad fiber, the same scanner in the probe module can be used for both the OCT image and the CSLO image and hence there is a cost saving in terms of scanning optics and also an inherent one-to-one pixel registration correspondence between the OCT and the CSLO images.

Once captured and guided by the double-clad fiber, both the single mode and the multi-mode optical waves will propagate backward along the double-clad fiber 106. At the multi-mode coupling region 110a, a relatively large portion of the multi-mode guided sample returned light (up to, for example, 50% for a typical single-stage multi-mode fiber coupler) can be extracted and channeled to confocal detector 120 for conversion from light intensity to an electrical signal.

Figure 3:
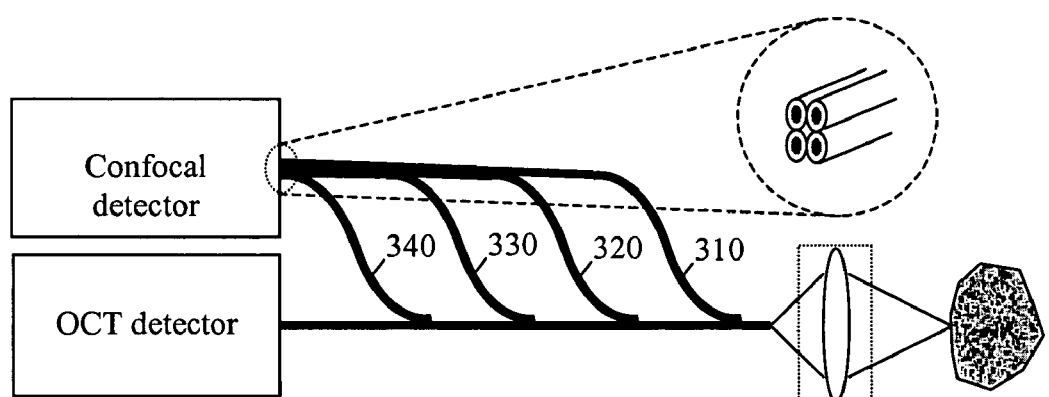
FIG. 3 shows an example of extracting a high percentage of the multi-mode guided optical power by cascading a multiple number of multi-mode couplers one after another and bundling the tap fibers together for sending the tapped optical power to a single detector.

A higher percentage of the multi-mode guided power can be extracted and sent to a single photo-detector 120 by a better design of the multi-mode coupler or by cascading a multiple number of standard multi-mode couplers one after another to tap 50% of the remaining optical power stage-by-stage as shown in FIG. 3. In fact, with 4 stages, a total of 50%+25%+12.5%+6.25%=93.75% of the guided multi-mode power can be tapped. By joining these pure multi-mode tap fibers (310, 320, 330, 340) into a bundle and directing the combined tapped multi-mode optical power simultaneously onto a single photo-detector, most of the multi-mode guided power meant for generating the CSLO signal can be converted into electrical signal.

Referring back to FIG. 1, the remaining multi-mode optical power in the double-clad will be further guided to the connection region 108a between the double-clad fiber 106 and the pure single mode fiber 102, where the remaining small amount of multi-mode optical power will radiate into the cladding of the pure single mode fiber 102 and be lost over a relatively short distance as well known to those skilled in the art. Meanwhile, the single-mode guided optical wave in the double-clad fiber 106 will be highly efficiently coupled to the pure single mode fiber 102 and sent back to the OCT detector within the OCT system 104 for OCT image generation. It should be noted that with the present design, the sample arm optical path length of the OCT interferometer should also include the optical path traveled by the single mode optical wave in the double-clad fiber 106 and the reference arm length of the OCT system should be selected accordingly.

Note that the presently invented way of collecting and guiding the sample-returned OCT and CSLO optical waves respectively in the single mode and multi-mode optical waveguides of a concentric dual-waveguiding structure offers a number of additional advantages. In addition to the fact that the invention enables simultaneous generation of the two images with one-to-one pixel correspondence and a high signal-to-noise ratio for both images, it also offers the possibility to substantially reduce the cost and to get rid of the complicated alignment issues associated with those combined systems disclosed previously. This is simply because multi-mode fiber couplers are inexpensive, optical fiber components do not require additional alignment, and the tapping multimode fibers can be easily bundled together and routed to a photo-detector with flexibility.

While the invention has been described with reference to the illustrated drawings and specific examples, it should be understood that the terms and examples used should be interpreted in a much broader sense. For example, the term OCT system used here is a general term that should be interpreted as covering all kinds of various OCT schemes, including time domain OCT (TD-OCT), spectral domain OCT (SD-OCT), and swept-source OCT (SS-OCT). In the claims, the term OCT detection device is intended to cover the detection subsystem in any of these OCT systems. The claims also use the term confocal microscope detection device which is intended to cover various flavors of confocal microscopes, including the preferred embodiment of a confocal laser scanning ophthalmoscope (CLSO). As another example, although the double-clad fiber shown has an outer core which is circular and concentric with the inner core, it should be understood that the term concentric is used in a more general sense and should be interpreted to cover the case where the concentricity is not exact and the cross-sectional shape of either the inner core 103 or the outer core 105 of the double-clad fiber 106 is not exactly circular. In fact, many double-clad fibers are manufactured for application in optically pumped fiber lasers and in such a case, it is desirable that the outer core of the double-clad fiber is not circular. These double clad fibers can also be used for the present invention.

Moreover, in the illustration of this invention, the double-clad fiber is depicted as having an outer cladding, it should be noted that this outer cladding does not have to be glass and in particular, this outer cladding can be air, a liquid or a highly reflective metal layer. Hence, any optical structure that can provide at least two waveguiding functions, one for single mode and another for multi-mode, can all be employed and the dual waveguiding structures do not need to be restricted to be concentric. In other words, the term dual-waveguiding structure should be interpreted as an optical structure having both single mode and multimode waveguiding capabilities that do not need to be limited to waveguide.

In addition, Mach-Zehnder and other interferometer layouts have been disclosed for OCT in which the illumination path is separate from the detection path [U.S. Pat. No. 6,485,413]. In reference to FIG. 1, an additional optical path is added to guide light from the low-coherence source within OCT system 104 to the sample 118. In this case, illustrated fibers would be used for only for collection.

Figure 4:
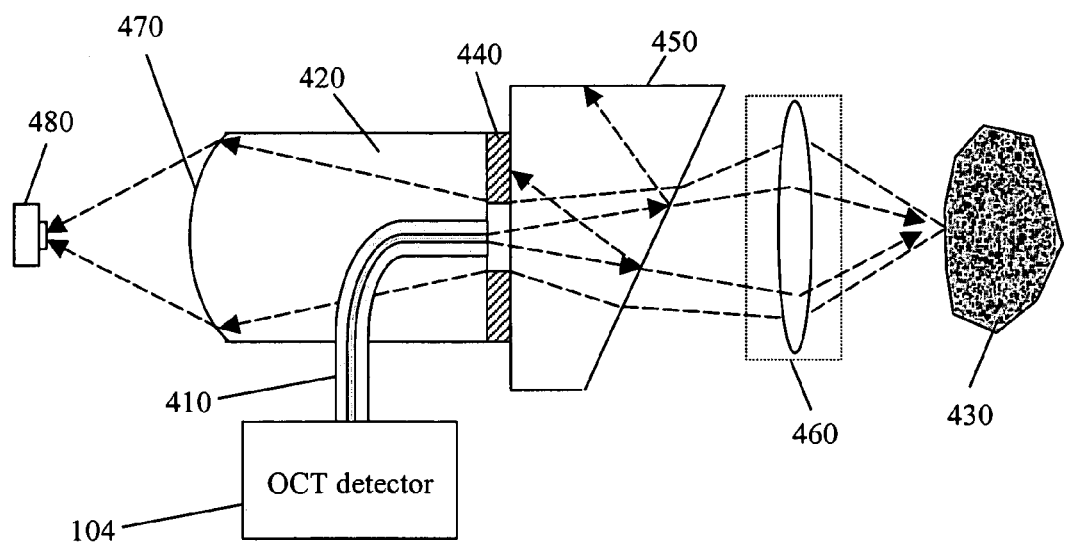
FIG. 4 shows an example of embedding a single mode fiber in a refractive index matched bulk optical lens module to guide the multi-mode optical power and send it to a photo detector.

For OCT imaging, it is highly desirable to use a single mode waveguide to collect the light reflected from the sample and deliver it to the detector. As noted above, for confocal microscope imaging, either a multi-mode or a single mode waveguide could be used for collection. In addition, it is also possible to collect the light for confocal detection without using a waveguide. An example of such an arrangement is shown in FIG. 4. As seen in FIG. 4, bulk optics can be used to collect light from an aperture concentric with the single mode fiber core. The bulk optics are configured to collect a large portion of the multi-mode energy and direct it a photo detector 480 of the confocal detection system. In the exemplary case of FIG. 4, a single mode fiber 410 is embedded in an optical bulk lens module 420 that has a focusing output surface which can be spherical or non-spherical. It is preferred that the refractive index of the optical bulk lens module 420 is matched to that of the cladding of the single mode fiber 410. The disturbance, by the fiber core 410, of the returned multi-mode optical wave on its way to detector 480, is minor due to the very small refractive index difference between the core and the cladding of the single mode fiber 410. The single-mode fiber is connected to an OCT system. A pin-hole 440 concentric with respect to the core of the single mode fiber 410 can be placed next to the lens module 420. A prism 450 can also be fixed next to the pin hole 440 and index match material can be used to fill the space between the fiber/lens module end surface and the prism 450. As mentioned before, the tilted or angled exit surface is used to ensure that the exit-optical-interface-reflected light is deflected away from and not captured. A probe module 460 guides the incident optical wave to the sample 430, and can be used for beam manipulating, including, for example, scanning and focusing. The sample-returned light wave will now be captured by both the core of the single mode fiber 410 which acts as a single-mode waveguide and also the lens module system 420 which acts as a multi-mode waveguide. The lens exit surface 470 acts as a multimode tapping device and focuses most of the multi-mode optical power guided by the lens module to a photo detector 480. To extract more guided multi-mode power to the photo detector 480, the exit surface 470 of the lens module 420 can be antireflection coated. Note that the lens module may have more than one refractive surface and it can also be made using refractive-index variation in a similar manner as that in a graded index rod or multi-mode fiber to achieve the light guiding and focusing function.

Meanwhile, it should be understood that the dual-waveguiding structure can have multiple overlapping or non-overlapping waveguides, including other multi-core waveguiding structures such as a multi-core fiber with some cores only supporting single-mode waveguiding and other cores supporting multi-mode waveguiding. It should also be understood that using a multi-mode fiber coupler to extract the multi-mode optical power is only one example of various ways to achieve the same goal. As is known to those skilled in the art, index matching material has been widely used for optical mode stripping and the same technique can also be used to extract the multi-mode power of the dual-waveguiding structure. Meanwhile, the double-clad fiber can also have its outer cladding removed through, for example, lapping and polishing, and a photo detector can be directly placed next to the exposed outer core for multi-mode optical power detection.

It should be noted that while the preferred embodiment uses a single light source for OCT and CSLO imaging, a separate light source can be provided for CSLO by injecting the second light source into core or cladding mode of fiber 106. This flexibility in choice of light sources allows use of a different wavelength or intensity for the CSLO illumination. The CSLO can even use multiple wavelengths to build a color image. The detection method of OCT ignores light from the CSLO source because that light is not coherent with the OCT reference beam. Alternatively, the OCT and CSLO light sources can have different wavelengths, with the each of the detectors sensitive only to the proper wavelength.

It should be noted that while the system has the capability to acquire CSLO and OCT images simultaneously, it could also be used in either an CSLO or OCT mode with the ability to switch between the modes by using either the OCT or the CSLO detector.

It also should be noted that the present invention can be used for various imaging applications. In addition to the imaging and diagnostics of a living eye, the present invention can also be used for other biological samples, especially those tissues inside the body of a living organism that require the use of an endoscope.

The foregoing description of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

The following references are incorporated herein by reference.

U.S. PATENT DOCUMENTS

U.S. Pat. No. 5,321,501, Swanson, E. A. et al. (1992) "Method and apparatus for optical imaging with means for controlling the longitudinal range of the sample"

U.S. Pat. No. 5,459,570, Swanson, E. A. et al. (1993) "Method and apparatus for performing optical measurements"

U.S. Pat. No. 5,975,697, Podoleanu, A. G. et al. (1998) "Optical mapping apparatus with adjustable depth resolution"

U.S. Pat. No. 6,485,413, Boppart, S. A. et al. (1998) "Methods and apparatus for forward-directed optical scanning instruments"

U.S. Pat. No. 6,769,769, Podoleanu, A. G. et al. (2002) "Optical mapping apparatus with adjustable depth resolution and multiple functionality"

US 2003/0199769, Podoleanu, A. et al. (2002) "Apparatus for high resolution imaging of moving organs"

US 2004/0233457, Podoleanu, A. G. et al. (2003) "Optical mapping apparatus with optimized OCT configuration"

US 2005/0140984, Hitzenberger, P. "Efficient optical coherence tomography (OCT) system and method for rapid imaging in three dimensions"

Co-pending application U.S. patent application Ser. No. 11/219,992, filed Sep. 6, 2005, Knighton, R. W., et al, "Enhanced optical coherence tomography for anatomical mapping"

OTHER PUBLICATIONS

Podoleanu, A. G. et al. (1997). "Simultaneous en-face imaging of two layers in the human retina by low-coherence reflectometry." *Optics Letters* 22(13): 1039-1041 Podoleanu, A. G. et al. (1998). "En-face coherence imaging using galvanometer scanner modulation." *Optics Letters* 23(3): 147-149

Podoleanu, A. G. et al. (1998). "Transversal and Longitudinal Images from the Retina of the Living Eye Using Low Coherence Reflectometry." *Journal of Biomedical Optics* 3(1): 12-20.

Podoleanu, A. G. et al. (1998). "Combined optical coherence tomograph and scanning laser ophthalmoscope." *Electronics Letters* 34(11): 1088-1090

Podoleanu, A. G. and D. A. Jackson (1999). "Noise Analysis of a Combined Optical Coherence Tomograph and a Confocal Scanning Ophthalmoscope." *Applied Optics* 38(10): 2116-2127

Fujimoto, J. G. et al. (2000) "Optical Coherence Tomography: An Emerging Technology for Biomedical Imaging and Optical Biopsy" *Neoplasia*, 2, 9-25

Rollins A. M. et al. (2002) "Emerging Clinical Applications of Optical Coherence Tomography" *Optics and Photonics News*, 13(4): 36-41

Fujimoto, J. G. (2003) "Optical coherence tomography for ultrahigh resolution in vivo imaging." *Nat Biotechnol* 21(11): 1361-1367

Hitzenberger, C. K. et al. (2003). "Three-dimensional imaging of the human retina by high-speed optical coherence tomography." *Optics Express* 11(21): 2753-2761

Podoleanu, A. G. et al. (2004). "Sequential optical coherence tomography and confocal imaging." *Optics Letters* 29(4): 364-366

Podoleanu, A. G., G. M. Dobre, et al. (2004). "Combined multiplanar optical coherence tomography and confocal scanning ophthalmoscopy." *Journal of Biomedical Optics* 9(1): 86-93

Sharp, P. F. et al (2004) "The scanning laser ophthalmoscope—a review of its role in bioscience and medicine" *Physics in Medicine and Biology* 49: 1085-1096

Yelin, D. et al. (2004). "Double-clad fiber for endoscopy." *Optics Letters* 29(20): 2408-2410.

We claim:

1. In a system for generating images of a sample which includes a confocal microscope detection device and an optical coherence tomography detection device and a light source for illuminating the sample, an arrangement for collecting light reflected from the sample comprising:
    a single mode waveguide collecting spatially coherent light reflected from the sample and directing the collected light to the optical coherence tomography detection device; and
    a second multimode waveguide collecting multimode light reflected from the sample and directing the collected light to the confocal microscope detection device and wherein the collecting end of the single mode waveguide is located concentrically within the collecting end of the multimode waveguide.

2. A system as recited in claim 1, wherein the single mode waveguide is a single mode optical fiber.

3. A system as recited in claim 2, wherein the multimode waveguide is a multimode optical fiber.

4. A system as recited in claim 1, wherein the ends of the single mode waveguide and the multimode waveguide that collect reflected light are in the form of a double clad fiber having a single mode core and multimode cladding.

5. A system as recited in claim 1, wherein the single mode waveguide also functions to couple light from the light source to the sample.

6. A system as recited in claim 5, further including a refractive-index-matched bulk optic in contact with the end of the single mode waveguide that collects reflected light for reducing the amount of light carried by the fiber from the source from reflecting back directly to the detector.

7. A system as recited in claim 1, wherein the multimode waveguide joins the single mode waveguide downstream from the light source.

8. A system as recited in claim 1, wherein the multimode waveguide further includes a tap for directing some of the light propagating in the multimode waveguide to the confocal microscope detection device.

9. A system as recited in claim 1, wherein the multimode waveguide further includes a plurality of taps for directing some of the light propagating in the multimode waveguide to the confocal microscope detection device.

10. A system as recited in claim 1, further including a pinhole adjacent the collection end of the second waveguide for controlling the numerical aperture of collection.

11. A system as recited in claim 1, further including a probe module positioned between the waveguides and the sample for focusing and scanning the light on the sample.

12. An apparatus for imaging a sample that has been illuminated by a light source comprising:
    an optical coherence tomography detection device;
    a confocal microscope detection device;
    a single mode optical fiber collecting spatially coherent light reflected from the sample and directing the collected light to the optical coherence tomography detection device; and
    a multimode optical fiber, one end of which collects multimode light reflected from the sample and direct the collected light to the confocal microscope detection device, and wherein the multimode fiber includes a first part that is formed concentrically around the single mode fiber near the collection end thereof and a second part in the form of a tap for directing a portion of the multimode light propagating in the first part of the multimode fiber and directing it to the confocal microscope detection device.

13. A system as recited in claim 12, further including a probe module positioned between the fibers and the sample for focusing and scanning the light on the sample.

14. A system as recited in claim 12, wherein the single mode fiber also functions to couple light from the light source to the sample. cladding and directing it to the confocal microscope detection device.

15. An apparatus for imaging a sample comprising:
    an optical coherence tomography detection device having a low coherence light source;
    a confocal microscope detection device;
    an optical fiber having a single mode core for coupling light from the light source to the sample and collecting spatially coherent light reflected from the sample and directing the collected light to the optical coherence tomography detection device, said optical fiber further having a multimode cladding extending along at least along a portion thereof arranged concentrically around the core and positioned to collect multimode light reflected from the sample; and
    a multimode tap fiber for directing some of the light propagating in the multimode cladding and directing it to the confocal microscope detection device.

16. An apparatus as recited in claim 15, further including a probe module positioned between the fibers and the sample for focusing and scanning the light on the sample.

17. In a system for generating images of a sample which includes a confocal microscope detection device and an optical coherence tomography detection device and a light source for illuminating the sample, an arrangement for collecting light reflected from the sample comprising:

a single mode waveguide collecting spatially coherent light reflected from the sample and directing the collected light to the optical coherence tomography detection device; and optics for collecting multimode light reflected from the sample and directing the collected light to the confocal microscope detection device and wherein said optics include a pinhole aperture surrounding said waveguide and a focusing element for directing the collected light to the confocal microscope detection device and wherein the waveguide is embedded in the focusing element.

18. A system as recited in claim 17, wherein the optics include a multimode waveguide.

19. A system as recited in claim 18, wherein the single mode waveguide is defined by the core of an optical fiber and the multimode waveguide is defined by a cladding formed about said core.

20. A system as recited in claim 17, wherein the single mode waveguide also functions to couple light from the light source to the sample.

21. A system as recited in claim 17, further including a probe module positioned between the single mode waveguide, the optics and the sample for focusing and scanning the light on the sample.

22. In a system for generating images of a sample which includes a confocal microscope detection device and an optical coherence tomography detection device and a light source for illuminating the sample, an arrangement for collecting light reflected from the sample comprising:

a single mode fiber waveguide collecting spatially coherent light reflected from the sample and directing the collected light to the optical coherence tomography detection device;

a bulk optical element in which the single mode fiber waveguide is embedded collecting multimode light reflected from the sample;

a pinhole aperture aligned with and surrounding the fiber waveguide for controlling the numerical collection aperture of the bulk optic; and a lens for directing the light collected by the bulk optical element to the confocal microscope detection device.

23. A system as recited in claim 22, wherein the lens is formed integrally with the bulk optic.

24. In a system for generating images of a sample with an apparatus that includes a confocal microscope detection device and an optical coherence tomography detection device and a light source for illuminating the sample, said method for collecting light reflected from the sample comprising:

collecting spatially coherent light reflected from the sample and directing the collected light to the optical coherence tomography detection device using a single mode optical waveguide; and collecting multimode light reflected from the sample with a multimode waveguide and directing the collected light to the confocal microscope detection device and wherein the single mode waveguide is defined by the core of an optical fiber and the multimode waveguide is defined by a cladding formed about said core.

25. A method as recited in claim 24, further including the step of focusing and scanning the illumination light on the sample.

* * * * *